United States Patent [19]

Roche et al.

[11] Patent Number: 5,460,825
[45] Date of Patent: Oct. 24, 1995

[54] TASTE MASK COATINGS FOR PREPARING CHEWABLE PHARMACEUTICAL TABLETS

[75] Inventors: Edward J. Roche, Paoli; Susan M. Papile, Blue Bell; Eleanor M. Freeman, Norristown, all of Pa.

[73] Assignee: McNeil-PPC, Inc., Milltown, N.J.

[21] Appl. No.: 96,791

[22] Filed: Jul. 23, 1993

Related U.S. Application Data

[63] Continuation of Ser. No. 777,872, Oct. 15, 1991, abandoned, which is a continuation-in-part of Ser. No. 528,003, May 23, 1990, Pat. No. 5,075,114, and Ser. No. 575,465, Aug. 30, 1990, abandoned.

[51] Int. Cl.⁶ ..................................................... A61K 9/26
[52] U.S. Cl. ........................ 424/470; 424/464; 424/482
[58] Field of Search ................................... 424/482, 464, 424/470

[56] References Cited

U.S. PATENT DOCUMENTS

| | | | |
|---|---|---|---|
| 4,180,559 | 12/1979 | Huber | 424/480 |
| 4,606,909 | 8/1986 | Bechgaard | 424/469 |
| 4,643,892 | 2/1987 | Peters et al. | 514/617 |
| 4,705,683 | 11/1987 | Dettman | 514/396 |
| 4,780,319 | 10/1988 | Zentner | 424/476 |
| 4,800,087 | 1/1989 | Mehta | 424/497 |
| 4,835,187 | 5/1989 | Reuter et al. | 514/570 |
| 4,835,188 | 5/1989 | Ho et al. | 514/570 |
| 4,837,030 | 6/1989 | Valorose | 424/490 |
| 4,837,031 | 6/1989 | Denton | 424/464 |
| 4,851,226 | 7/1989 | Julian | 424/482 |
| 4,894,233 | 1/1990 | Sharma et al. | 514/960 |
| 4,900,558 | 2/1990 | Barry | 424/470 |
| 4,915,949 | 4/1990 | Wong | 424/468 |
| 4,915,953 | 4/1990 | Jordan | 424/472 |
| 4,940,588 | 7/1990 | Sparks | 424/464 |
| 4,946,686 | 8/1990 | McClelland | 424/482 |
| 5,075,114 | 12/1991 | Roche | 424/470 |
| 5,215,755 | 6/1993 | Roche et al. | 424/480 |
| 5,260,072 | 11/1993 | Roche et al. | 424/464 |

FOREIGN PATENT DOCUMENTS

| | | |
|---|---|---|
| 0317274 | 5/1981 | European Pat. Off. . |
| 0040696 | 12/1981 | European Pat. Off. . |
| 0279976A1 | 8/1988 | European Pat. Off. . |
| 0411952A2 | 2/1991 | European Pat. Off. . |
| 229110 | 9/1990 | Japan . |
| 2166651A | 5/1986 | United Kingdom . |

OTHER PUBLICATIONS

Database WPIL Week 8838, Derwent Abstract No. AN-88-266524 for Japanese Patent Publication JP-A-63 192 725 (Shinetsu Chem Ind KK), Derwent Publications Ltd. (1988).

*Primary Examiner*—Thurman K. Page
*Assistant Examiner*—William E. Benston, Jr.

[57] ABSTRACT

Chewable medicament tablets are made from coated rotogranules of a medicament wherein the rotogranules are formed from a granulation mixture of: medicament, e.g. famotidine; binder, e.g. HPMC; and carrier, e.g. lactose; and the rotogranules are coated with cellulose acetate, cellulose acetate butyrate or a combination thereof and hydroxypropyl cellulose. A process for making such tablets and a method of providing taste masking of medicaments utilizing such coated rotogranules.

6 Claims, No Drawings

TASTE MASK COATINGS FOR PREPARING CHEWABLE PHARMACEUTICAL TABLETS

This is a continuation of application Ser. No. 07/777,872, filed Oct. 15, 1991, now abandoned which is a continuation-in-part of application Ser. No. 07/528,003, filed May 23, 1990, now U.S. Pat. No. 5,075,114, and application Ser. No. 07/575,465, filed Aug. 30, 1990, now abandoned.

FIELD OF THE INVENTION

This invention relates to tablets containing means to mask the taste of active ingredients. More particularly, the taste masking of active ingredients is achieved by rotogranulating active material with a binder and carrier material and coating such rotogranulations with a taste masking polymer coating.

BACKGROUND OF THE INVENTION

Orally administered medicaments are given to the patient in many forms, such as liquid solutions, emulsions, or suspensions, or in solid form such as capsules or tablets (as used herein, the term "tablet" means any shaped and compressed solid dosage form, including caplets). Medicaments administered in tablet or capsule form are usually intended to be swallowed whole. Therefore, the often disagreeable taste of the active ingredient need not be taken into account in formulating the medicine, except for the provision of means to prevent the taste from being apparent during the short time that the medicine is in the mouth. Such means may include the provision of an appropriately thin and quickly dissolving coating on the tablet, the use of the gelatin capsule form (the gelatin outer shell of the capsule keeps the active ingredient inside until the capsule has been swallowed), or simply compressing a tablet firmly so that it will not begin to disintegrate during the short time that it is intended to be in the mouth.

Children, older persons, and many other persons have trouble swallowing whole tablets and even capsules. Therefore, in cases where the dosage to be administered cannot be made into a very small tablet or capsule, it is desirable to provide the medicine either in liquid form or in a chewable solid form, in addition to the tablet or capsule that is designed to be swallowed whole. Even where the medicine can be formulated as a liquid, it is desirable also to be able to provide a chewable solid form (i.e. tablets) because of added convenience versus carrying a supply of liquid medicine.

A common problem with chewable tablet forms is the often disagreeable taste of the active ingredient which manifests itself during chewing. In some cases, the taste of the active medicament in a tablet can be overpowered by adding flavoring ingredients to the tablet so that when it is chewed, the taste of the active ingredient is simply overpowered. For instance, this has been done with children's aspirin where the dosage is small enough so that the amount of flavoring agents needed to mask the taste of the medicine is not so great that the tablet becomes unreasonably large. A different approach is taken with a commercially available children's size tablet of acetaminophen (acetyl para-aminophenol or "APAP") wherein the APAP is present in granules that are coated with ethyl cellulose. A significant proportion of the APAP remains shielded by the coating (and therefore does not contribute to taste) while the tablet is in the mouth, despite some breakage of the ethyl cellulose coating during compression of the tablet and some additional breakage of the coating during chewing. The APAP becomes bioavailable via permeation through the coating (although ethyl cellulose is not soluble in aqueous fluids, water does permeate through the coating) and from the granules where the coating is broken.

U.S. Pat. No. 4,851,226, issued Jul. 25, 1989, discloses chewable medicament tablets wherein granules of active ingredient are directly coated with a blend of cellulose acetate or cellulose acetate butyrate and polyvinylpyrrolidone. While such direct coating of pharmaceutical active with this polymer blend may be acceptable for certain applications, e.g. taste masking of active particles which are smooth and of uniform size, it has been found to be unacceptable as applied to active compositions whose raw granules are small and irregularly shaped such as famotidine because of poor dissolution and taste masking results.

Co-pending U.S. patent application Ser. No. 389,645, filed Aug. 4, 1989, abandoned in favor of Continuation-in-Part application Ser. No. 686,723, now U.S. Pat. No. 5,215,755, discloses chewable medicament compositions comprising a rotogranulation blend of from about 88 to about 97.5% medicament, about 2 to about 10% polyvinylpyrrolidone (PVP) and about 0.5 to about 2.0% sodium lauryl sulfate (SLS), by weight of the weight of the total composition. In further embodiments a coating of hydroxyethyl cellulose (HEC) or a mixture of hydroxyethyl cellulose and hydroxypropyl methylcellulose (HPMC) is added to these rotogranulated particles. The HEC and HEC/HPMC coatings provide excellent taste masking while still permitting acceptable bioavailability of the active ingredient including poorly water soluble (at low pH) ibuprofen.

The present invention is directed to the discovery of a granulating and coating process for active medicaments which can achieve a better balance between taste masking, dissolution and rate of bioavailability when applied to irregularly shaped raw granules of compositions like famotidine than other previously known coating combinations.

SUMMARY OF THE INVENTION

As embodied and fully described herein, the present invention provides a medicament comprising a rotogranulation composition comprising about 4 to 10% of a binder material, about 10 to 94% of a carrier material and about 2 to 85% of an active material by weight of the total rotogranulation and a coating for such rotogranulation comprising a polymer coating comprising a blend of one or both of cellulose acetate (CA) or cellulose acetate butyrate (CAB) and hydroxypropyl cellulose (HPC), preferably, the polymer blend comprises from about 3 to about 50 weight percent of HPC by weight of the total weight of the polymer blend. In preferred embodiments of the invention, the coated rotogranulated medicament is included in a chewable tablet. The CA and/or CAB:HPC coating may also provide for sustained release in addition to taste masking of the coated medicament.

In further preferred embodiments, the coated medicament comprises: a medicament selected from the group consisting of famotidine, loperamide, cimetidine and ranitidine, more preferably famotidine of a particle size in the range of about 5 to 75 microns. The medicament is rotogranulated with a binder, preferably selected from the group consisting of PVP, starch or hydroxypropyl methyl cellulose (HPMC), more preferably HPMC with a particle size range of 50 to 150 microns; a carrier composition such as fine particle size lactose, fructose, mannitol, sucrose, dextrose, maltodextrins, confectioner's sugar or mixtures thereof, more preferably lactose with a particle size of between 5 to 75 microns to produce a granulation which is substantially spherical in shape. The rotogranulated medicament is coated with about 5% to 20% and preferably about 11% by weight of the total weight of the coated particles with CA and/or CAB:HPC, preferably about an 70:30 blend of CA:HPC. The coated particles are then compressed into tablet form together with excipients and flavoring agents to produce chewable tablets.

The invention also provides a process using the coated rotogranulated particles to make chewable tablets.

DETAILED DESCRIPTION OF THE INVENTION

The invention will now be described specifically in terms of its most preferred embodiments which are the preparation of rotogranulations of famotidine and chewable tablets comprising coated rotogranules of famotidine. Famotidine is a histamine $H_2$-receptor antagonist useful for inhibiting gastric secretion and treating ulcers. Uncoated famotidine has an unpleasant or bitter taste absent its proper barrier separation or masking from the mouth. Reference will also be made in detail herein to other preferred embodiments of the compositions, processes and methods of the invention.

In accordance with preferred embodiments of the invention granules of medicament, preferably raw famotidine, HPMC and lactose are rotogranulated with water to produce nearly spherical granulated particles. These rotogranulated particles are preferably in the size range of about 150 to 400 microns.

The rotogranulation is preferably formed by blending about 2 to 85% by weight raw famotidine with about 4 to 10% by weight HPMC and about 10 to 94% by weight of lactose. Percentages by weight are by weight of the total rotogranulation composition.

Details of a preferred process of rotogranulating and subsequent fluid-bed coating are provided in the examples section. Preferred methods are further described in: Jones, D. M. "Factors to Consider in Fluid-Bed Processing," *Pharmaceutical Technology*, April 1985, Pg. 50–63; and Jager, K. F. et al., "Effect of Material Motion on Agglomeration in the Rotary Fluidized-Bed Granulator", *Drugs Made in Germany*, Vol. XXV, Pg. 61–65 (1982). The entire disclosure of these articles are hereby incorporated herein by reference. Granulations comprising famotidine, HPMC and lactose produced by rotogranulation in accordance with the invention are nearly spherical in shape and will be referred to hereinafter as "rotogranules".

Rotogranules have increased strength due to the compaction or densification of the granulation mixture as rotogranules are formed by rotation in the rotogranulator bed. The famotidine rotogranules have excellent integrity and enough strength to withstand fluid bed coating processes without significant breakage. This resistance to breakage is advantageous since broken particles are of a smaller size and are not readily coated in subsequent coating steps. Smaller sized particles without proper coating detract from the taste masking purpose of the coating by providing poor taste to the mixture as a whole. Further, smaller sized particles tend to agglomerate and interfere with subsequent fluid bed coating operations.

The irregular and small particle size of famotidine raw granules are undesirable for direct coating because such small particles may escape coating and/or the irregularly shaped particles require a higher amount of coating to completely cover the entire surface of the granule. Such high and uneven amounts of coating results in poor dissolution and taste mask properties. It has been found in accordance with the present invention that rotogranulation of raw famotidine with lactose and HPMC produce spherical particles, which are readily coated to provide good taste mask and dissolution properties thereto.

HPMC acts as a binder in the granulation process. Use of HPMC as a binder imparts good mechanical strength to the granules.

Lactose is a carrier which adds bulk and smoothness to the body of the granules and may increase the release rate and dissolution of the only slightly water soluble famotidine. Other useful carrier materials which may be substituted for lactose include other saccharides, e.g. fructose, sucrose, dextrose, confectioner's sugar and maltodextrins. The carrier materials should be of fine particle size, preferably in the range of 5 to 75 microns to fill in surface voids and provide a smooth surface to the rotogranule.

Further, microcrystalline cellulose may be blended into such carrier materials and incorporated into the rotogranules. Fine particle size microcrystalline cellulose may be added to such carrier materials in the range of about 5–20% of such materials to provide increased strength to the rotogranules.

In preferred embodiments of the compositions and processes of the invention, medicament, preferably famotidine in rotogranular form, with binder and carrier ingredients, is coated with a blend of CA and/or CAB:HPC polymer. The coated rotogranules, together with other ingredients such as flavoring agents, extenders, excipients, and the like, are compressed into tablet form. (As used herein, the term "rotogranule" refers to individual rotogranulated particles.)

Cellulose acetate and cellulose acetate butyrate are quite water insoluble but are soluble in organic solvents. They can provide good taste masking properties since they do not dissolve in the mouth and are tough enough to remain effectively intact during processing and normal chewing in the mouth. If used alone, however, a coating of CA and/or CAB would not provide adequate bioavailability of the active ingredient after swallowing the chewed tablet. To provide the requisite bioavailability, hydroxypropyl cellulose (HPC) is added to the coating mixture. HPC is a polymer which is soluble in both water and organic solvents. The water solubility of HPC provides bioavailability of the coated active medicament in the gastrointestinal (GI) tract. When the coated granules are swallowed, the active medicament becomes bioavailable via permeation as the coating disintegrates.

Permeation can occur through the intact coating but is encouraged by the disintegration of the coating which becomes porous through dissolution of the water soluble HPC. The coating system utilized herein for rotogranules is disclosed in co-pending U.S. patent application Ser. No. 528,003, filed May 23, 1990, now U.S. Pat. No. 5,075,114, which discloses a coating for raw active (not rotogranulated) medicament comprising a polymer blend of cellulose acetate and/or cellulose acetate butyrate and water soluble hydroxypropyl cellulose to provide a taste masked and/or sustained release coating. The entire disclosure of this reference is hereby incorporated herein by reference.

The CA and/or CAB:HPC polymer blend also has good mechanical flexibility which is advantageous in a product where the coating must withstand the forces of tablet compression and chewing in the mouth. A high enough proportion of CA and/or CAB and HPC coating remains effectively intact on the famotidine rotogranules through the compression of the tablet and through normal chewing in the mouth to permit effective taste masking of the unpleasant tasting famotidine. The term "effectively intact" means that the coating remains sufficiently integral to mask the taste or flavor of the medicament. This taste masking is effective to mask the unpleasant flavor of the medicament without requiring large and bulky amounts of overpowering flavoring agents.

The HPC and CA and/or CAB blends of this invention have been found to be more versatile than the PVP blends of Julian and Radebaugh discussed earlier and the parent application hereof, i.e., U.S. Ser. No. 575,465, now U.S. Pat. No. 5,260,072 the entire disclosure of which is hereby incorporated herein by reference. Due to the superior flexibility of HPC polymer as compared to PVP, higher percentages of HPC (up to 50%) can be used than is recommended by Julian and Radebaugh for PVP (3 to 30%). Higher amounts of the water soluble component HPC increases the rate and extent of disintegration of the coating thus increasing the porosity of the coating. Presence of such higher amount of the water soluble component HPC advantageously increases the bioavilability of the coated medicaments.

The solubility of HPC in organic solvents permits ready mixing with CA or CAB during the production of the coated granules, since CA and CAB are not very soluble, if at all, in water, and are more conveniently applied from an organic solvent solution. HPC and CA and/or CAB form clear compatible solutions in organic solvents, preferably acetone/methanol mixtures, which are suitable for pharmaceutical coating. The blend of CA and/or CAB and HPC provides the balance needed for good taste masking while being chewed in the mouth, along with either rapid or sustained bioavailability of the active medicament in the GI tract after swallowing. Generally the ratio of CA and/or CAB to HPC is in the range of about 95:5 to 50:50, preferably the coating is about 70:30; CA:HPC.

The coated granules may be made by coating the rotogranules of medicament with an organic solvent solution of the polymers in a fluidized bed coating operation. A wide variety of organic solvents may be used to prepare the organic solvent solution of the coating polymers. For instance, a preferred solvent is acetone-methanol, but other solvent systems may also be used, including methylene chloride-methanol (e.g. 9:1), acetone-ethanol, acetone-ethyl acetate, toluene-ethanol, and others. As a general rule, the proportion of polymer in the solvent solution will be from about 5 to 20 and preferably 8 to 15 weight percent for optimal taste masking and rapid release of drug depending upon the specific solvents used and other similar considerations. As a practical matter, a concentration of less than 5% CA and/or CAB and HPC polymer blend would unduly lengthen the coating process and a concentration of more than 14% would hamper spraying of the thickened solution.

The polymers are dissolved in the solvent and the polymer solution is then coated onto famotidine rotogranules or other medicament active ingredient or combination of ingredients, using a fluidized bed coater. Air (which may be heated) passes through a bed of the medicament granules to fluidize them, and the solvent solution of the two polymers is sprayed onto the fluidized bed and thereby coats the rotogranules. The air passing through the bed dries the coated rotogranules, so that a dry coated granule is obtained. The coated granules are then used in combination with various excipients, flavors, and colors to make a chewable tablet.

The dried coating usually constitutes about 5–20% of the total dry weight of the coated rotogranule. The exact proportions of coating to medicament desired for individual cases can be determined by routine experimentation. The amount of coating may be varied in light of the intended application and desired bulk of the products. Chewable tablets can be acceptable in larger sizes than swallowed tablets since chewing will reduce the size of the tablets in the mouth. Larger proportions of coating may be used to provide a sustained release or better tasting formulation.

When two or more medicaments are utilized in tablets of the present invention the coatings may be varied to provide a slower release of one medicament over another. This is especially advantageous for dosing a combination of medicaments that are more effectively released in different parts of the digestive tract or are better released separately in the digestive tract to avoid interference with each other or other incompatibility. Further, the same medicament may be subject to different coating compositions and amounts to provide for sustained release of some portion of the medicament and immediate release of another portion of the medicament to achieve an optimal dosing versus time profile. Obtaining such optimal dosing/time profiles depends upon the particular medicaments and medical needs required. The exact proportions of coating materials used to achieve these profiles can be determined by routine experimentation.

While exact size of the coated rotogranules has not been found to be critical, the coated granules, are preferably sized in the range of 150 to 400 microns. Particle sizes of less than 150 microns are difficult to coat and particle sizes of greater than 400 microns may provide undesirable grittiness to the finished product. In general, particles of like size facilitate blending and provide regularity to dosage forms.

In addition to famotidine, other solid low bulk, low water soluble medications in need of taste masking can be used in accordance with the the invention. Illustrative additional examples include loperamide, cimetidine and ranitidine their pharmaceutically acceptable salts and combinations thereof and with other medicaments. Identification of medicaments herein is intended to apply to pharmaceutically acceptable salts thereof as well. Further, the coating of the invention provides a convenient means for providing a viable dosage form for combination medicaments which are incompatible before (e.g. during storage) or after administration.

An illustrative preferred procedure for coating the rotogranules of medicament in accordance with the invention is briefly described here and provided in more detail in the following examples section. The medicament, in rotogranular form, is preferably placed in a fluidized bed coater and is fluidized by a flow of warm air. The temperature of the air has not been found to be narrowly critical, and can vary over a wide range, keeping in mind the fact that the temperature should not be high enough to cause decomposition, sintering, or melting of the medicament granules. When coating famotidine rotogranules, a product temperature of from about 25° to 50° C. is maintained. The rate of air flow is adjusted so as to fluidize the granules. Such flow will vary depending on factors such as the specific equipment used, the size of the charge of granules, the size of the individual granules, the apparent specific gravity of the granules, and other factors that are known to those skilled in the art of fluidized bed coating.

After the medicament has been fluidized, the polymer solution is sprayed via bottom, top or tangential spray onto the fluidized bed. The air flow through the bed is continued until the amount of solvent remaining in the coating has been greatly reduced. The rotogranules are actually dry to the touch within a very short time after the coating solution has been sprayed onto the granules of medicament; a matter of a few seconds in some cases. The total drying time required to ensure that the solvent content of the coating has been reduced to the level desired may take much longer, depending on the solvent used, temperature of the air, size of the batch, and the like. Routine experimentation will suffice to determine the appropriate air temperatures and total times required in the fluidized bed coaters in individual cases.

The invention will now be illustrated by examples. The examples are not intended to be limiting of the scope of the present invention but read in conjunction with the detailed and general description above, provide further understanding of the present invention and an outline of a process for preparing the rotogranule compositions and chewable medicament tablets of the invention.

EXAMPLES

The Examples below set forth the ingredients and proportions for typical laboratory scale preparations of coated medicament granules. The materials used are the following:

Famotidine—in the form of granules having a particle size of between about 5 to 75 microns;

HPMC—in the form of a cream-colored powder having a particle size of about 50 to 150 microns.

HPC—Hydroxypropyl cellulose having a molecular weight of about 80,000 to about 370,000. Suitable PC includes those available from Aqualon in the grades known by the tradenames KLUCEL EF, LF, JF or GF.

CA—in the form of a white powder.

Lactose—white to cream colored powder having a particle size of between 5 and 75 microns.

The coating methods used are disclosed for example in Jones, D. M. "Factors to Consider in Fluid-Bed Processing" *Pharmaceutical Technology,* April 1985 and rotogranulating methods are taught by, for example, in Jager, K. F. et al., "Effect of Material Motion on Agglomeration in the Rotary Fluidized-Bed Granulator", *Drugs Made in Germany,* Vol. XXV, Pp. 61–65 (1982) which have been incorporated herein by reference. The term "total coat" refers to the proportion of coating to uncoated rotogranule in the coated rotogranule product, concentration of "polymer solution" to the proportion of polymer in the organic solvent solution, and "total batch" to the weight of medicament plus coating.

EXAMPLE I

Rotogranulation/Coating of Famotidine

Rotogranulation: Combine 5.2 kg of famotidine, 2.4 kg of HPMC (2910 USP, 5 CPS METHOCEL* E5 premium) and 32.4 kg of lactose impalpable in a rotogranulator bowl.

Rotogranulate by spraying water (approximately 14 kg) at a rotor speed of 400–500 RPM. Dry the rotogranulated particles to a product temperature of 30°–35° C. after decreasing the rotor speed to 250 RPM.

Particle Coating: Coat the particles produced in the rotogranulation step in a Wurster Coating apparatus. The polymer coating solution should consist of a 10% by weight solution of cellulose acetate 398–10 (39.8% acetyl content—10 seconds viscosity) and HPC (hydroxypropyl cellulose, KLUCEL EF) where the ratio of CA to HPC is 70:30. The solvent used is an 80/20 mixture of acetone/methanol. Apply 11% by weight polymer to the particles. Maintain product temperature at about 30° C. (106° F.) during the coating step.

EXAMPLE II

The procedure of Example I is carried out except that 1 kg of loperamide is substituted for 5.2 kg of famotidine and the amounts of lactose is increased to 36.6 kg.

EXAMPLE III

The functions of several ingredients utilized in example III and some typical replacements for them are as follows:

Mannitol is a sweetener which can be replaced by dextrose, fructose, sorbitol, compressible sugar, and/or lactose;

Microcrystalline cellulose is used as a binder, and can be replaced with other binders such as alginic acid, carboxymethyl cellulose, hydroxypropylmethylcellulose, PVP, or starch;

Aspartame is an artificial sweetener which can be replaced with others such as saccharin;

Magnesium stearate is a lubricant (to lubricate the dye walls and punches used during the tablet compression procedure). It can be replaced by talc, stearic acid, calcium stearate, zinc stearate, leucine, glycerides, sodium stearyl fumarate or the like; and Artificial and natural flavor agents can be any conventional artificial and natural flavoring agents and flavor enhancers such as vanilla, grape, peppermint, orange, cherry, and/or spearmint flavors and conventional flavor enhancers or sweeteners.

PREPARATION OF CHEWABLE TABLETS

The ingredients displayed below were sieved, dry blended, and compressed by standard procedures into round (disc shaped) chewable tablets, each weighing 385 mg. Each tablet contained 10 mg. of active famotidine per tablet from coated rotogranules prepared in accordance with the procedure of Example 1 containing 11 weight percent CA:HPC; 70:30 coating.

EXAMPLE IX

| Component | mg/Tablet |
| --- | --- |
| Famotidine, USP | 10 |
| HPMC 2910 USP (METHOCEL* E5 Prem.) (Granulation) | 4.62 |
| Lactose | 62.31 |
| Cellulose acetate | 6.65 |
| Hydroxypropyl cellulose USP (coating) | 2.85 |
| TOTAL WEIGHT OF COATED ROTOGRANULES | 86.43 |

| Ingredients and kg approximate weights | mg/Tablet | Per Batch, |
| --- | --- | --- |
| Coated Particles | 86.43 | 17.29 |
| Mannitol USP, FL2080 | 259.33 | 51.87 |
| Microcrystalline Cellulose (e.g. Avicel PH-101) | 30 | 6.00 |
| Aspartame | 2.5 | 0.500 |
| Prosweet Powder (Sugarless) | 1.23 | 0.246 |
| Magnesium Stearate, NF | 3.85 | 0.770 |
| Flavoring | 1.54 | 0.308 |
| Coloring | 0.12 | 0.024 |

-continued

| Ingredients and kg approximate weights | mg/Tablet | Per Batch, |
|---|---|---|
| TOTAL TABLET WEIGHT | 385 mg | 77.00 kg |

The scope of the present invention is not limited by the description, examples and suggested used herein and modifications can be made without departing from the spirit of the invention. For example, other components may be added to the tablets including additional actives, various flavorings, preservatives and other pharmaceutical excipients. The present invention may also be used to provide a chewable form for vitamins, minerals or other nutrients.

Application of the compositions and processes of the present invention for medical and pharmaceutical uses can be accomplished by any clinical, medical and pharmaceutical methods and techniques as are presently and prospectively known to those skilled in the art. Thus it is intended that the present invention cover the modifications and variations of this invention provided that they come within the scope of the appended claims and their equivalents.

What is claimed is:

1. A process of preparing a chewable medicament tablet comprising the steps of:
   rotogranulating a composition of in the range of from about 2 to about 85 percent of a medicament, in the range of from about 4 to about 10 percent of a binder and a in the range of from about 10 to about 94 percent of a fine particulate carrier having a particle size from about 5 to about 75 microns to provide granules;
   coating the granules with a polymer blend composed of a polymer selected from the group consisting of cellulose acetate, cellulose acetate butyrate and a combination of both blended with hydroxypropyl cellulose to form coated granules; and
   forming a chewable tablet by compressing the coated granules with tableting excipients.

2. The process of claim 1 wherein the polymer blend has a weight ratio in the range of about 95:5 to 50:50 of a polymer selected from the group consisting of cellulose acetate, cellulose acetate butyrate and a combination thereof to hydroxypropyl cellulose.

3. The process of claim 2 wherein the polymer blend comprises about an 70:30 blend of cellulose acetate:hydroxypropyl cellulose and comprises about from 5 to 20% by weight of the total weight of the coated rotogranulation composition.

4. A method for taste masking medicaments comprising rotogranulating a medicament with hydroxypropylmethylcellulose and a fine particulate lactose having a particle size from about 5 to about 75 microns to form granules and coating the granules with a taste masking effective amount of polymer blend composed of a polymer selected from the group consisting of cellulose acetate, cellulose acetate butyrate and a combination thereof blended with hydroxypropyl cellulose.

5. The method of claim 4 wherein the medicament is selected from the group consisting of famotidine, loperamide, cimetidine, ranitidine, salts thereof and combinations thereof.

6. The method of claim 4 wherein the medicament is famotidine.

* * * * *